US00PP16217P2

(12) United States Plant Patent
Hansen

(10) Patent No.: US PP16,217 P2
(45) Date of Patent: Jan. 24, 2006

(54) ***HOSTA* PLANT NAMED 'HANKY PANKY'**

(50) Latin Name: *Hosta hybrida*
Varietal Denomination: Hanky Panky

(75) Inventor: Hans Andrew Hansen, Waseca, MN (US)

(73) Assignee: Shady Oaks Nursery, LLC, Waseca, MN (US); Part Interest ( * ) Notice: Subject to any disclaimer, the term of this patent is extended or adjusted under 35 U.S.C. 154(b) by 95 days.

(21) Appl. No.: 10/995,681

(22) Filed: Nov. 23, 2004

(51) Int. Cl.
*A01H 5/00* (2006.01)

(52) U.S. Cl. ..... Plt./353

(58) Field of Classification Search ..... Plt./353
See application file for complete search history.

*Primary Examiner*—Anne Marie Grunberg
(74) *Attorney, Agent, or Firm*—Penny J. Aguirre

(57) ABSTRACT

A new cultivar of *Hosta* hybrid *Hosta* 'Hanky Panky', a sport of *Hosta* 'Striptease', characterized by its unique variegated foliage with spring foliage having dark green centers and light green margins with a stripe of white that occurs at the junction of the center and the margin. The foliage changes in late summer and fall progresses and matures to a pattern having light centers with a deep green area replacing the white stripe area and greyed-yellow margins.

2 Drawing Sheets

Botanical classification: *Hosta hybrida.*
Cultivar designation: 'Hanky Panky'.

BACKGROUND OF THE INVENTION

The present invention *Hosta* 'Hanky Panky', relates to a new and distinct cultivar of *Hosta,* botanically known as a *Hosta* hybrid, hereinafter referred to as 'Hanky Panky'.

The inventor discovered the new cultivar, 'Hanky Panky', in summer of 1999 in a tissue culture lab in Waseca, Minn. 'Hanky Panky' originated as a sport of *Hosta* 'Striptease' (unpatented) that arose during micropropagation. 'Hanky Panky' was selected for its unique variegated leaf pattern. The spring foliage of 'Hanky Panky' has dark green centers and wide light green margins with a stripe of white that occurs at the junction of the center and the margin. The foliage undergoes several color and pattern changes as the season progresses and matures to a pattern having lighter green to yellow centers with a deep green area replacing the white stripe area with greyed-yellow margins. 'Striptease', the parent plant, differs from 'Hanky Panky' in having light green centers with dark margins and is similar in having the white stripe pattern between the margins and centers.

Asexual reproduction of the new cultivar was first accomplished by in vitro propagation in Waseca, Minn. in fall of 2002. Asexual reproduction of the new cultivar by division and tissue culture has shown that the unique features of 'Hanky Panky' are stable and reproduced true to type in successive generations.

SUMMARY OF THE INVENTION

The following traits have been repeatedly observed and represent the characteristics of the new cultivar. These attributes in combination distinguish 'Hanky Panky' as a new and unique cultivar of *Hosta* as observed for a period of four years.

1. The spring foliage of 'Hanky Panky' has variegated foliage with light green margins, deep green margins, and a white stripes between the centers and margins. 'Striptease', the parent plant has foliage with a similar white stripe pattern but with light green centers and dark green margins (reversed).
2. The foliage of 'Hanky Panky' changes as the season progresses with the margins and centers becoming lighter green and more yellow and deep green areas that replace the white stripe pattern in the area between the centers and the margins.
3. 'Hanky Panky' reaches a height of about 33 cm (13 inches), exclusive of flower scapes, and a spread of about 83 cm (33 inches) at maturity. 'Hanky Panky' is slightly smaller in overall dimensions to 'Striptease'.
4. 'Hanky Panky' blooms for about 3 to 4 weeks from early July to late August with pale lavender flowers, similar to 'Striptease'.

BRIEF DESCRIPTION OF THE DRAWING

The accompanying colored photographs illustrate the overall appearance and distinct characteristics of the new *Hosta.* The photographs were taken of mature plants of 'Hanky Panky' as grown outdoors in Waseca, Minn. for three years.

Figure 1:
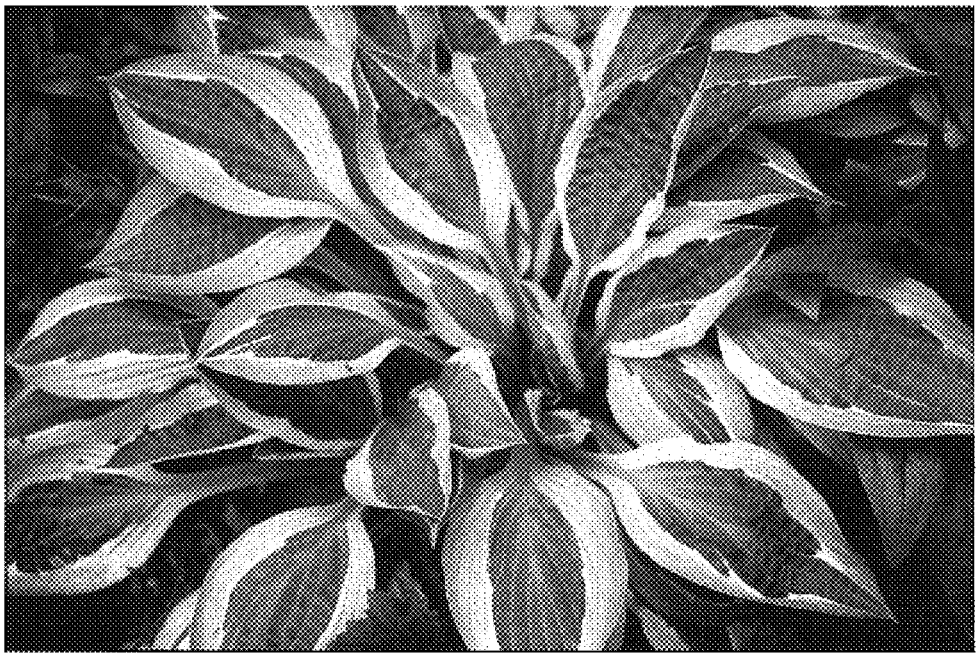
FIG. 1 was taken in June and provides an overall view of the spring foliage of the new cultivar.
Figure 2:
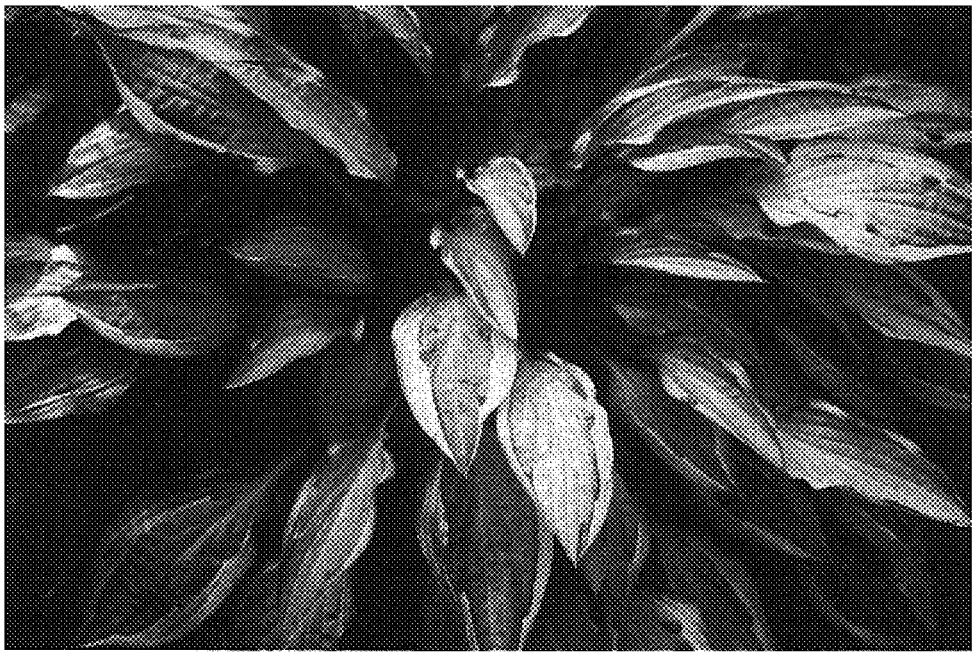

The photograph in FIG. 2 was taken in September and provides a view of the progression of change in variegation pattern that is present in fall.

The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of 4 year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Hanky Panky' is a cultivar of *Hosta* of hybrid origin.

Parentage: Sport of *Hosta* 'Striptease' (not patented).

General description:

*Blooming period.*—About 3 to 4 weeks from early July to early August.

*Plant habit.*—Herbaceous perennial, clump-forming, mounded foliage of medium size.

*Height and spread.*—Reaches about 33 cm (13 inches) in height (without bloom stocks) and about 83 cm (33 inches) in width.

*Hardiness.*—Zone 3–8.

*Culture.*—Light shade to medium shade, moist soils of moderate fertility.

*Diseases and pests.*—No susceptibility or resistance to diseases or pests has been observed for 'Hanky Panky'.

*Root description.*—Freely branched, fleshy.

*Propagation.*—In vitro propagation is the preferred method utilizing typical methods for *Hosta,* division are also possible.

*Root development.*—Rooted transplants from tissue culture fully develop in a 96-cell liner in about 6 to 8 weeks in a greenhouse with average temperatures of about 70° F.

*Growth rate.*—Vigorous.

Foliage description:

*Leaf shape.*—Ovate.

*Leaf division.*—Simple.

*Leaf base.*—Cuneate.

*Leaf apex.*—Acute to slightly acuminate.

*Leaf venation.*—About 6 pairs of veins, camptodrome pattern, color matches leaf coloration.

*Leaf margins.*—Entire, slightly wavy.

*Leaf attachment.*—Petiolate.

*Leaf arrangement.*—Basal, radiate spirally from base.

*Leaf surface.*—Upper and lower: glabrous.

*Leaf color.*—Young leaves (upper surface): centers between 144A and 144B, margins 145A, white stripe 155B (between margin and center). Young leaves (lower surface): centers 144B, margins 145B, white stripe 155B. Spring foliage (upper surface); centers between 137A and 137B, margins range from 145A to 145D, white stripe 155B. Spring leaves (lower surface): centers 137B, margins range from 145B to 145D, white stripe 155B. Mature leaves (upper and lower surface): changes throughout late summer and fall; 1.) centers become lighter green 144A and margins darken to 137A to 137B, white stripe 155B 2.) centers become mottled with a blend of 144A and 144B, margins 137A to 138B, white stripe 155B 3.) centers gradually turn more yellow with a blend of 144A and 144B and 11C, margins becomes greyed-yellow 162D, white stripe is replaced with green area 138B.

*Leaf variegation pattern.*—Centers for young foliage and spring foliage average about 4 cm with margins from 1.25 to 2.5 cm and a white stripe between the centers and margins of about 1 to 3 mm, margins narrow as leaves mature to an average of 0.5 to 1 cm with white stripe replaced with green area averaging 1 to 4 mm and often extending into apex of centers.

*Leaf size.*—About 18 cm (7 inches) in length, up to about 7.6 cm (3 inches) in width.

*Leaf quantity.*—About 5 to 7 per shoot (eye).

*Petiole size.*—Up to about 18 cm in length, about 0.8 cm in width.

*Petiole color.*—New foliage; inner and outer surface 145A, mature foliage; centers 144B with margins 138A to 138B.

*Petiole shape.*—Sulcate.

Flower scape description:

*Scape shape.*—Round, solid.

*Scape number.*—One per mature eye under normal growing conditions.

*Scape posture.*—Straight, held upright at about 80 to 90° from horizontal.

*Scape size.*—About 58 cm (23 inches) in length, up to about 4 mm in width.

*Scape color.*—144B.

*Scape surface.*—Glaucous.

*Leaf bracts.*—1 per scape, 144B in color, ovate in shape, average of 2.5 cm in length and 1.2 cm in width.

Flower description:

*Inflorescence type.*—Terminal racemes on elongated flower scapes.

*Lastingness of inflorescence.*—About 3 to 4 weeks from first opening bloom to fading of last opening bloom, individual blooms last about one week.

*Flower shape.*—Tubular.

*Flower fragrance.*—None detected.

*Flower bud shape.*—Spathulate.

*Flower size.*—Fully open: about 4.5 cm in length and about 2.5 cm in width.

*Flower color.*—76C (pale lavender).

*Pedicels.*—About 1 mm in diameter, 2 mm in length, 144B in color.

*Perianth features.*—Comprised of 6 tepals, 3 interior and 3 exterior, overlapping in expanded region and fused in tube region.

Reproductive organs:

*Gynoecium.*—1 Pistil, stigma is 1-lobed, ovary is compound and composed of 3 locules.

*Androcoecium.*—6 stamens, anthers have versatile attachment, pollen was not observed.

*Seed.*—Sterile, seeds are not produced.

I claim:

1. A new and distinct cultivar of *Hosta* plant named 'Hanky Panky' as herein illustrated and described.

* * * * *